US005622179A

United States Patent [19]
Pfandal et al.

[11] Patent Number: 5,622,179
[45] Date of Patent: Apr. 22, 1997

[54] HOLDING PLATE FOR MEDICAL EQUIPMENT

[75] Inventors: Peter Pfandal, Harr; Bernd Thurau, Hoslwang, both of Germany

[73] Assignee: PVB Medizintechnik GmbH, Kircheseeon/Eglharting, Germany

[21] Appl. No.: 249,030

[22] Filed: May 25, 1994

[30] Foreign Application Priority Data

May 28, 1993 [DE] Germany .......................... 43 17 985.1

[51] Int. Cl.$^6$ .................................................. A61B 19/00
[52] U.S. Cl. ............................. 128/897; 73/756; 128/675
[58] Field of Search ................ 128/897–98, 673–75, 128/DIG. 12, DIG. 13; 604/65–67; 312/209; 73/756

[56] References Cited

U.S. PATENT DOCUMENTS

| | | | |
|---|---|---|---|
| 4,970,900 | 11/1990 | Shepherd et al. | 128/675 |
| 5,280,789 | 1/1994 | Potts | 128/673 |

FOREIGN PATENT DOCUMENTS

| | | |
|---|---|---|
| 3145310C2 | 5/1983 | Germany . |
| 1238879 | 7/1971 | United Kingdom . |

OTHER PUBLICATIONS

"Transpac", Brochure published by the Abbott Company.

Primary Examiner—Angela D. Sykes
Assistant Examiner—John P. Lacyk
Attorney, Agent, or Firm—Cushman, Darby & Cushman IP Group of Pillsbury Madison & Sutro LLP

[57] ABSTRACT

The holding plate for medical equipment, in particular for medical blood pressure measuring, blood withdrawal, infusion and transfusion apparatuses which have a plate-like fixing device with which they can be fixed to the holding plate, has two parallel guide tracks (3, 4) with grooves (4, 5; 27, 28) for accommodation of the plate-like fixing device. At least one of the grooves (4, 5) has a stop (13). A spring-pretensioned (6) catch stud (10) protrudes from the holding plate (1), the stop (13) and the catch stud (10) having a distance between them, based on the longitudinal direction of the guide tracks (3, 4), which corresponds to the length of the plate-like fixing device.

29 Claims, 4 Drawing Sheets

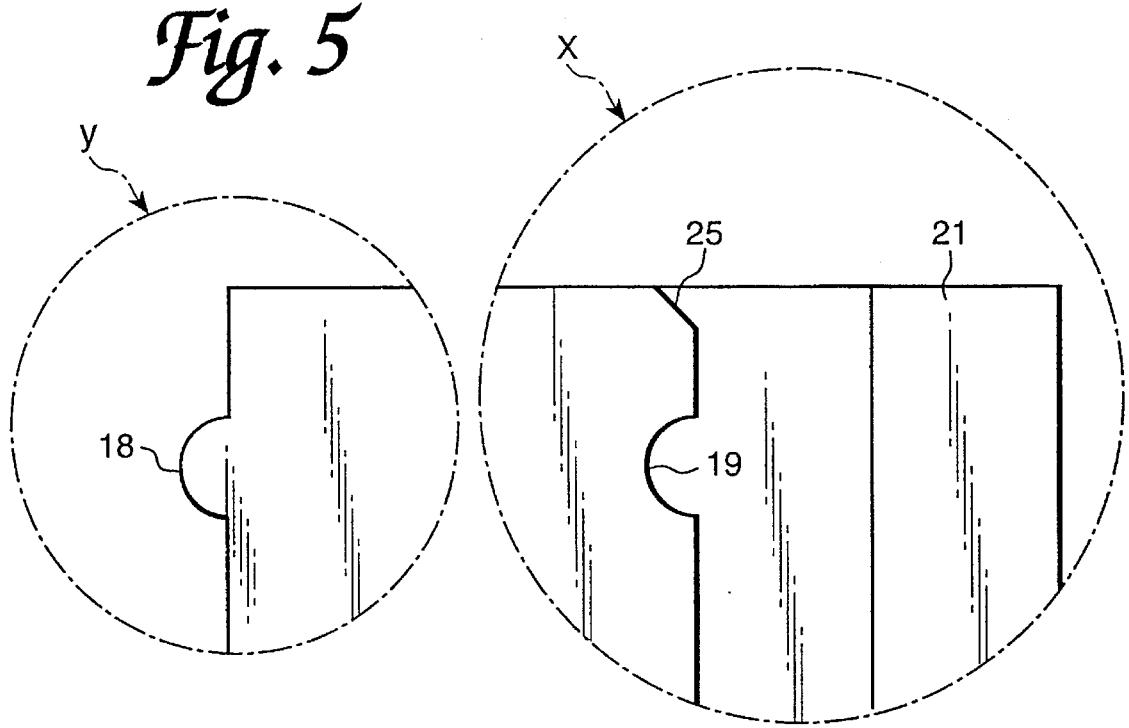

HOLDING PLATE FOR MEDICAL EQUIPMENT

BACKGROUND OF THE INVENTION

1. Field of the Invention

The invention relates to a holding plate for medical equipment, in particular for medical blood pressure measuring, blood withdrawal, infusion and transfusion apparatuses which have a plate-like fixing device with which they can be fixed to the holding plate.

2. Description of the Related Art

A conventional holding plate is known from the brochure from the company ABBOTT entitled "TRANSPAC", the 3rd generation disposable transducer.

During medical care and monitoring of patients, various systems must be connected to the patient, such as e. g. various blood pressure measuring apparatuses (so-called transducers), infusion apparatuses, blood withdrawal apparatuses etc. These individual apparatuses are fixed to a tubular infusion stand, each apparatus being provided with its own holding plate. Several holding plates can be pushed against one another in module form and fixed to one another with a snap holder. For fixing the medical equipment to the holding plate, a snap closure is also provided there, which engages with two catch studs into longitudinal holes of a plate-like fixing device on the medical equipment and locks this.

This medical equipment is usually used only once and disposed of after use. With the known holding plates, it is scarcely possible in practice to detach the medical equipment from the holding plate and also to separate from one another several holding plates fixed to one another by means of the snap holder. In practice, these are therefore also disposed of together with the medical equipment intended for a single use. This causes unnecessary costs for acquisition and disposal of the holding plates, especially since medical equipment must be treated as "special waste", so that disposal is very expensive.

SUMMARY OF THE INVENTION

The object of the invention is to improve the holding plate of the abovementioned to the extent that medical equipment fixed to it can be detached easily, without destruction and without tools, so that it can be reused. It should also be possible for several holding plates coupled to one another to be separated from one another easily, without destruction and without tools.

This object is achieved by the features described in patent claim 1. Advantageous embodiments and further developments of the invention can be seen from the sub-claims.

Summarizing, in the invention, the medical equipment is inserted into guide tracks and held securely in their position by a catch stud pretensioned by a spring. By pressing the catch stud down, the medical equipment can be removed effortlessly from the guide track, so that the holding plate can be used again. In a corresponding manner, several holding plates can be coupled to one with a type of groove and spring connection on guide tracks positioned on the side, and can be separated from one another easily and without tools. A catch system is also provided here.

BRIEF DESCRIPTION OF THE DRAWINGS

The invention is described in more detail below with the aid of embodiment examples in connection with the drawings. In the drawings:

FIGS. 4 and 5 show enlarged details X and Y of FIG. 1;

The same reference numbers in the individual figures describe components which are the same or correspond to one another in function.

DETAILED DESCRIPTION OF THE PRESENTLY PREFERRED EMBODIMENTS

Figure 1:
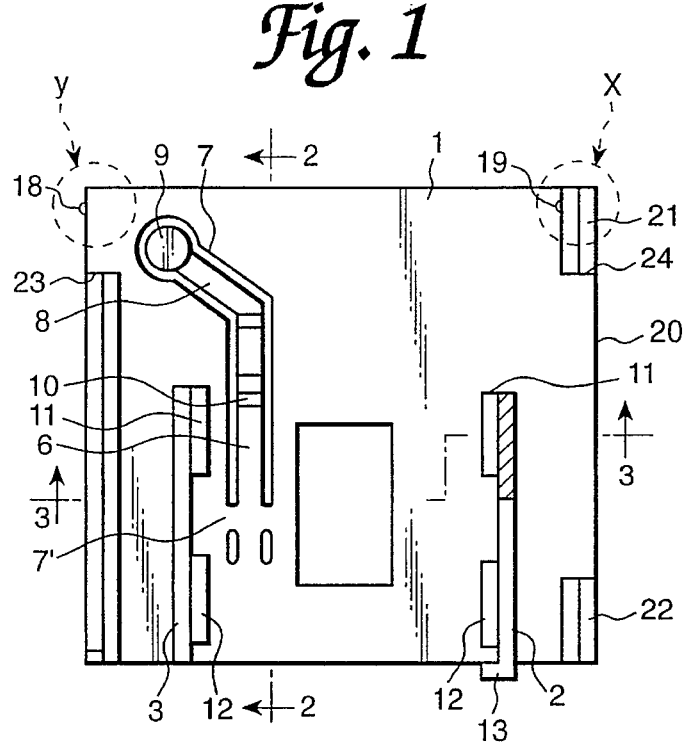
FIG. 1 shows a plan view of a holding plate according to a first embodiment example of the invention.
Figure 2:
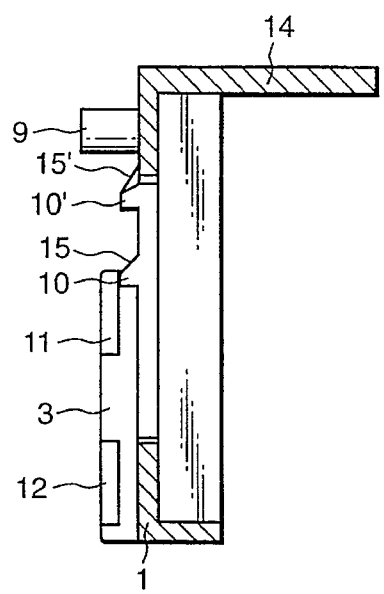
FIG. 2 shows a section along line 2—2 in FIG. 1.
Figure 3:
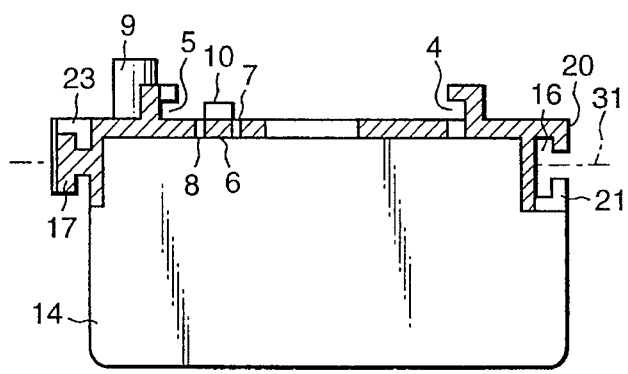
FIG. 3 shows a section along line 3—3 in FIG. 1.

The embodiment example of FIGS. 1 to 3 shows a rectangular holding plate 1, from the surface of which protrude two parallel guide tracks 2 and 3 which have an L-shaped cross-section (cf. FIG. 3), so that, between the upper side of the holding plate 1 and the guide tracks 2 or 3, in each case a groove 4 or 5 is formed, into which a plate-like fixing device (not shown) on the medical equipment can be pushed. The reciprocal distance between the guide tracks 2 and 3 corresponds here to the width of the plate-like fixing device. A spring 6 is constructed in the plane of the holding plate 1, and in particular by slots 7 which run on both sides of the spring, so that the spring 6 is formed in one piece from the material of the holding plate. The spring 6 here is located in the region between the two guide tracks 2 and 3, and in the embodiment example of FIG. 1 it lies asymmetrically with respect to the central line and closer to one guide track 3. The spring 6 has an angled arm 8 facing the nearest outer edge of the holding plate 1, onto the end of which arm a push-button protruding from the surface of the holding plate 1 is constructed. The angled arm 8 is long enough for the push-button 9—with respect to the sliding direction of the guide tracks—to lie outside a region formed by their extensions. The plate-like fixing device can therefore be guided past the push-button 9 without problems. The slots 7 running on both sides of the spring 6 are interrupted in a region 7' close to the firmly clamped end of the spring, which gives the clamping of the spring a better stability, since the bending forces on the clamped end of the spring can be transmitted better into the material of the holding plate 1 and local stresses can be distributed more uniformly.

From the spring 6, a catch stud 10 protrudes beyond the surface of the holding plate 1, the edge of the catch stud facing the fixing region lying between the guide tracks being at right angles to the surface of the holding plate and the edge facing away therefrom having a slanted surface 15 (FIG. 2). When the medical equipment is pushed in, its plate-like fixing device presses against the slanting buffer 15, which bends the spring 6 and allows the apparatus to be pushed into the guide tracks 3 and 4. When the equipment has been pushed in completely, the catch stud is freed and the spring 6 presses this in the direction of the medical equipment, so this is secured against being pulled out.

The guide tracks 2 and 3 have—as mentioned—L-shaped limbs, which, however, do not extend over the entire length of the guide tracks but only over certain sections 11 and 12 at the two ends of the guide tracks. In the region in between, the guide tracks have only a bar protruding perpendicularly from the holding plate 1. This measure serves to reduce frictional forces.

In the insertion direction, at least one of the guide tracks, in the embodiment example of FIG. 1 guide track 2, has on its end a stop 13 which projects here beyond the outer contour of the holding plate 1 and covers the groove 4.

The medical equipment is thus fixed between the stop 13 and the catch stud 10 in the sliding direction, the distance between the stop 13 and the catch 10 stud corresponding to the length (based on the insertion direction of the plate-like fixing device) of the medical equipment.

To detach the medical equipment from the holding plate 1 again, the push-button 9 is pressed downwards, whereupon the catch stud 10 releases the plate-like fixing device, after which the medical equipment can be pulled out of the guide tracks 2 and 3.

The holding plate is provided on two opposite edges with coupling devices which allow several such holding plates to be coupled to one another laterally. According to the invention, this is effected by a groove and tongue connection which, in the embodiment shown here, is constructed by a groove 16 having a T-shaped cross-section (FIG. 3) and a corresponding tongue 17 having a T-shaped cross-section. Instead of the T-shaped cross-section, a dovetail cross-section can also be used.

The groove 16 is constructed such that its sections arranged symmetrically with respect to a central line 31 of the groove do not overlap in the longitudinal direction (parallel to the sliding direction; cf. FIG. 1). The L-shaped limb 20—on top with respect to the central line 31—lies symmetrically with respect to the centre of the sliding direction, but does not extend over the entire length of the holding plate 1. Adjacent L-shaped limbs 21 and 22—on the bottom with respect to the central line 31—are correspondingly provided immediately adjacent to the ends of the L-shaped limb 20. This measure serves to reduce frictional forces and to facilitate reciprocal sliding of the holding plates.

The T-shaped tongue 17 on the other side of the holding plate 1 likewise does not extend over the entire length of the holding plate 1 but only over the total of the lengths of the upper L-shaped limb 20 and one of the lower L-shaped limbs 21. The one end of the T-shaped tongue 17 thus forms a stop 23 which, when two holding plate are joined, pushes against a counter-stop 24 formed by the corresponding end of the upper L-shaped limb 20.

To prevent unintentional sliding of two holding plates coupled to one another, a catch projection 18 and a catch recess 19 are provided. The catch projection 18 is provided here on the outside of the holding plate in the extension of the T-shaped tongue 17. The corresponding catch recess 19 is provided in the region of the lower L-shaped limb 21, and in particular in the free space which is open at the top and lies in the extension of the upper L-shaped limb 20.

The catch projection 18 and the catch recess 19 are shown as detail in FIGS. 5 and 4. The two are in the form of a universal joint and have, for example, a diameter of 0.5 mm. Because of the intrinsic elasticity of the plastic material of the holding plate, the catch projection 18 and the catch recess 19 can snap into one another in the end position, but can be detached again manually without applying a relatively large amount of force.

As can be seen from FIG. 4, the corner of the holding plate adjacent to the catch recess 19 is provided with a bezel 25 which facilitates insertion of the T-shaped spring 17.

Figure 6:
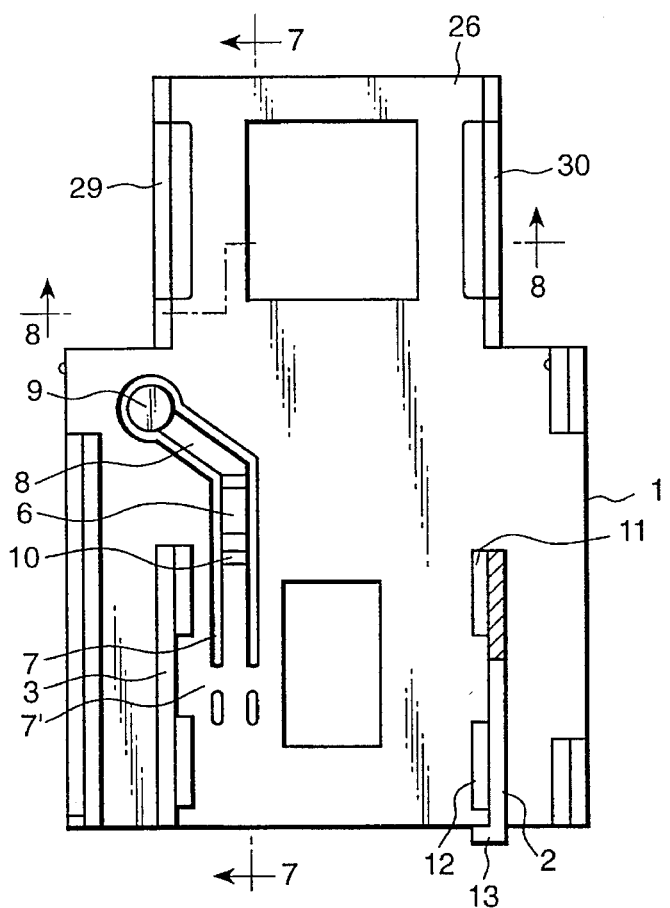
FIG. 6 shows a plan view of a holding plate according to a second embodiment example of the invention.
Figure 7:
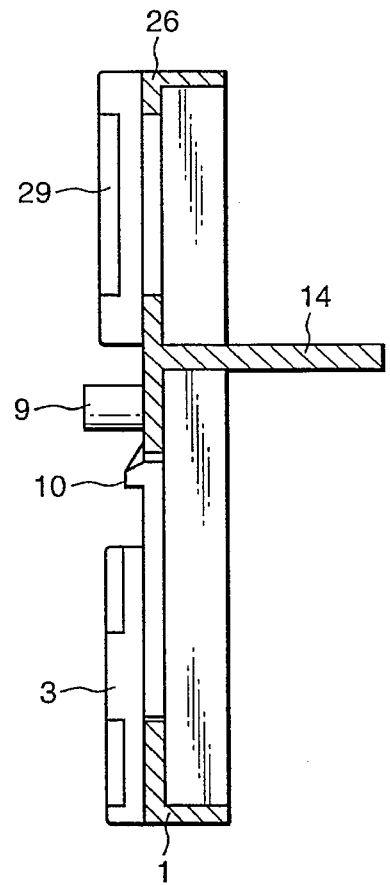
FIG. 7 shows a section along line 7—7 in FIG. 6.
Figure 8:
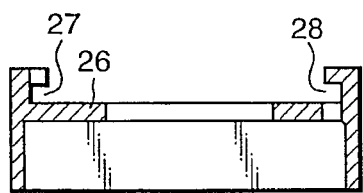
FIG. 8 shows a section along line 8—8 in FIG. 6.

FIGS. 6 to 8 show a second embodiment example of the invention, which differs from that of FIGS. 1 to 3 in that the holding plate has a rectangular extended piece 26 for accommodating further medical equipment. This extended piece has a pair of guide tracks 29, 30 which are located in an extension of the guide tracks 2 and 3 and align with these. These guide tracks also form grooves 27, 28, corresponding to the grooves 4 and 5. The extended piece 26 is narrower than the holding plate of FIGS. 1 to 3 and extends transversely to the insertion direction only up to the outsides of the guide tracks 29 and 30, that is to say does not have the groove and tongue connection 16, 17. In the embodiment example shown, no additional locking is provided for this medical equipment fixed to the extended piece 26. Apparatuses which are coupled to the medical equipment held between the guide tracks 2 and 3 will usually be held there, so that additional fixing is not necessary.

The holding plate 1 of both embodiment examples has a holding bar 14 which protrudes perpendicularly from its under-side facing away from the guide tracks and can be attached to an infusion stand by means of a clamping device, which is not shown. This clamping device grips the holding bar 14 like pliers, for which the clamping device has, for example, a groove into which the holding bar 14 can be pushed and can then be secured by one or more screws. Preferably, this clamping device can be swivelled relative to the infusion stand, so that it can be fixed in any desired or at least several given swivelled positions—relative to an axis lying perpendicular to the longitudinal axis of the infusion stand.

Figure 9:
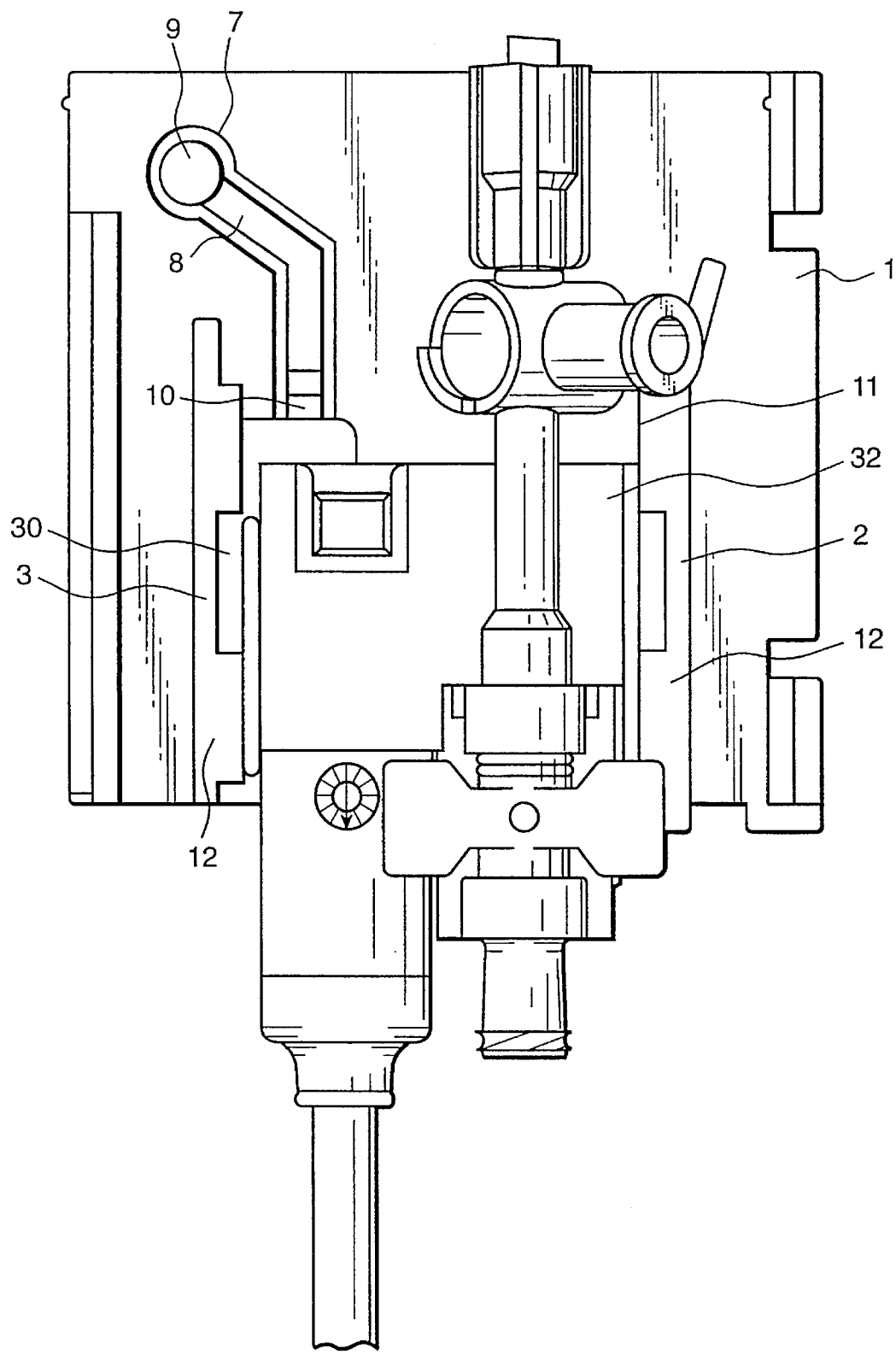
FIG. 9 shows a plan view of the combination of the holding plate, medical device and fixing device attached thereto.

FIG. 9 illustrates holding plate 1 according to the first embodiment having a plate-like fixing device 30 inserted into the groove defined by guide tracks 2 and 3. In the fully inserted position shown in FIG. 9, catch stud 10 engages an end of fixing device 30. The other end of fixing device 30 engages stop 13 (see FIG. 1). A medical device 32 is attached to fixing device 30 which is attached to holding plate 1 as described above. Thus, medical device 32 is detachably secured to holing plate 1 via fixing device 30.

What is claimed is:

1. A holding plate for securing medical equipment thereto, wherein said medical equipment is attached to a fixing device that is adapted to be attached to the holding plate, said holding plate comprising:

a base having a main surface;

two parallel guide tracks located on said base, each of said guide tracks defining a guide track groove adapted to receive said fixing device responsive to said fixing device being inserted into said grooves;

a stop associated with said guide tracks adapted to engage one end of said fixing device responsive to said fixing device being inserted into said guide tracks; and a spring attached to said base and having a catch stud located on a main surface of said spring, said catch stud adapted to engage another end of said fixing device responsive to said fixing device being inserted into said guide tracks, said catch stud and said stop being separated from one another by a distance corresponding to a length of said fixing device, wherein said spring is integral with said base and is positioned relative to said base such that, in a non-deflected state, said main surface of said spring is flush with said main surface of said base.

2. A holding plate as defined in claim 1, wherein said stop is located at an end of said guide tracks.

3. A holding plate as defined in claim 2, wherein said stop projects beyond an outer contour of said base.

4. A holding plate as defined in claim 3, wherein said spring includes an angled arm and a push-button located at a free end of said angled arm, wherein said push-button projects from said base and lies outside a region of said base over which said fixing device is slid in order to insert said fixing device in said guide tracks.

5. A holding plate as defined in claim 1, wherein said catch stud has a slanted surface so that as said fixing device is inserted into said guide tracks, said spring is deformed by said fixing device.

6. A holding plate as defined in claim 1, wherein said guide tracks includes end portions having an L-shaped cross-section and a central region defined by a bar protruding perpendicularly from said base.

7. A holding plate as defined in claim 1, wherein said base includes a groove defined therein and located at one side thereof and a tongue located at an opposite side thereof, said groove and said tongue of adjacent bases cooperating with one another to form a groove and tongue connection for coupling said adjacent bases.

8. A holding plate as defined in claim 7, wherein said groove and said tongue have a T-shaped cross-section.

9. A holding plate as defined in claim 8, wherein said groove is formed from L-shaped limbs arranged symmetrically with respect to a central plane of said groove provided in said base, and said L-shaped limbs are displaced with respect to one another along a longitudinal direction of said groove such that said L-shaped limbs do not overlap on another.

10. A holding plate as defined in claim 9, wherein said L-shaped limbs include:
 a first L-shaped limb arranged symmetrically with respect to a longitudinal axis of said base and parallel to said guide tracks;
 a second L-shaped limb arranged adjacent to said first L-shaped limb at a first end thereof; and
 a third L-shaped limb arranged adjacent to said first L-shaped limb at a second end thereof.

11. A holding plate as defined in claim 10, wherein said tongue has a length corresponding to the sum of the length of said first L-shaped limb and the length of one of said second and said third L-shaped limbs, and wherein said holding plate further comprises a second stop formed at an end of said tongue said second stop interacting with a corresponding end of said first L-shaped limb of an adjacent base.

12. A holding plate as defined in claim 11, wherein a corner of said base adjacent to one of said second and said third L-shaped limbs is provided with a bezel to facilitate insertion of a corresponding tongue of an adjacent base into a channel defined by one of said second and said third L-shaped limbs.

13. A holding plate as defined in claim 9, further comprising:
 a catch projection located at one side of said base; and
 a corresponding recess located at the other side of said base, said catch projection and said corresponding recess detachably securing adjacent bases to one another in a snap-fit relationship.

14. A holding plate as defined in claim 1, further comprising a holding bar protruding perpendicularly from a plane defined by said base for fixing said base to an infusion stand.

15. A holding plate as defined in claim 1, further comprising:
 an extended piece protruding from said base in a direction generally parallel to said guide tracks; and
 extension guide tracks located on said extended piece and aligned with said guide tracts.

16. A holding plate as defined in claim 15, wherein a width of said extended piece, measured perpendicularly to a longitudinal axis of said guide tracks, is narrower than a longitudinal length of said base.

17. A holding plate as defined in claim 2, wherein said spring comprises an angled arm integral with said base, said angled arm lying in a plane defined by said base and including a push-button located at a free end thereof, wherein said push-button projects from said base and lies outside a region of said base over which said fixing device is slid in order to insert said fixing device in said guide tracks.

18. A holding plate as defined in claim 17, wherein said catch stud has a slanted surface so that as said fixing device is inserted into said guide tracks, said spring is deformed by said fixing device.

19. A holding plate as defined in claim 18, wherein said base includes a groove located at one side thereof and a tongue located at an opposite side thereof, said groove and said tongue of adjacent bases cooperating with one another to form a groove and tongue connection for coupling adjacent bases.

20. A holding plate as defined in claim 19, further comprising:
 a catch projection located at one side of said base; and
 a corresponding recess located at an opposite side of said base, said catch projection and said corresponding recess detachably secure said bases to one another in a snap-fit relationship.

21. A holding plate as defined in claim 20, further comprising a holding bar protruding perpendicularly from base for fixing said base to an infusion stand.

22. A holding plate as defined in claim 21, further comprising:
 an extended piece protruding from said base in a direction generally parallel to said guide tracks; and
 extension guide tracks located on said extended piece and aligned with said guide tracks.

23. A medical equipment securing system comprising:
 a fixing device to which said medical equipment is attached; and
 a holding plate to which said fixing device is selectively attached, said holding plate comprising:
  a base;
  two parallel guide tracks located on said base, each of said guide tracks defining a guide track groove for receiving said fixing device therein;
  a stop associated with said guide tracks engaging one end of said fixing device; and
  a spring attached to said base and having a catch stud located thereon, said catch stud engaging another end of said fixing device, said catch stud and said stop being separated from one another by a distance corresponding to a length of said fixing device, wherein said spring is integral with said base and lies in a plane defined by said base.

24. A medical equipment securing system as defined in claim 23, wherein said stop is located at an end of said pair of guide tracks and projects beyond an outer contour of said base.

25. A medical equipment securing system as defined in claim 23, wherein said spring includes an angled arm and a push-button located at a free end of said angled arm, wherein said push-button projects from said base and lies outside a region of said base over which said fixing device is slid in order to insert said fixing device in said guide tracks.

26. A medical equipment securing system as defined in claim 23, wherein said catch stud has a slanted surface so that as said fixing device is inserted into said guide tracks, said spring is deformed by said fixing device.

27. A medical equipment securing system as defined in claim 23, wherein said base includes a groove located at one side thereof and a tongue located at an opposite side thereof, said groove and said tongue of adjacent bases cooperating with one another to form a groove and tongue connection for coupling said adjacent bases.

28. A medical equipment securing system as define in claim 23, further comprising:

a catch projection located at one side of said base; and a corresponding recess located at the other side of said base, said catch projection and said corresponding recess detachably securing adjacent bases to one another in a snap-fit relationship.

29. A medical equipment securing system as define in claim 23, further comprising:

an extended piece protruding from said base in a direction generally parallel to said guide tracks; and extension guide tracks located on said extended piece and aligned with said guide tracks.

* * * * *

UNITED STATES PATENT AND TRADEMARK OFFICE
CERTIFICATE OF CORRECTION

PATENT NO. : 5,622,179
DATED : April 22, 1997
INVENTOR(S) : Peter Pfandl, et. al.

It is certified that error appears in the above-identified patent and that said Letters Patent is hereby corrected as shown below:

Title page,

Please change:

item "[19] Pfandal et al" to --[19] Pfandl et al.-- item "[75] Inventors: Peter Pfandal,..."

to --[75] Inventors: Peter Pfandl,....--

Signed and Sealed this

Thirteenth Day of January, 1998

Attest:

BRUCE LEHMAN

*Attesting Officer*     *Commissioner of Patents and Trademarks*